United States Patent [19]
Beck, Jr. et al.

[11] Patent Number: 5,632,748
[45] Date of Patent: May 27, 1997

[54] ENDOSTEAL ANCHORING DEVICE FOR URGING A LIGAMENT AGAINST A BONE SURFACE

[75] Inventors: Charles L. Beck, Jr.; E. Paul France, both of Salt Lake City; Richard L. Ellingson, Draper, all of Utah

[73] Assignee: Linvatec Corporation, Largo, Fla.

[21] Appl. No.: 361,868

[22] Filed: Dec. 22, 1994

Related U.S. Application Data

[63] Continuation of Ser. No. 76,390, Jun. 14, 1993, abandoned.

[51] Int. Cl.$^6$ .................... A61B 17/58; A61F 5/00
[52] U.S. Cl. .................... 606/89; 606/96; 606/72; 606/232
[58] Field of Search .................... 606/72, 73, 75, 606/86–87, 88–89, 151, 213, 215–218, 232; 623/13; 411/71, 75, 78, 79

[56] References Cited

U.S. PATENT DOCUMENTS

| | | | |
|---|---|---|---|
| 3,832,931 | 9/1974 | Talan | 411/71 |
| 3,953,896 | 5/1976 | Treace | |
| 3,988,783 | 11/1976 | Treace | |
| 4,011,602 | 3/1977 | Rybicki et al. | |
| 4,301,551 | 11/1981 | Dore et al. | 267/152 |
| 4,464,076 | 8/1984 | Leibhard | 411/79 |
| 4,520,511 | 6/1985 | Gianezio et al. | |
| 4,590,928 | 5/1986 | Hunt et al. | |
| 4,632,100 | 12/1986 | Somers et al. | |
| 4,662,886 | 5/1987 | Moorse et al. | 623/13 |
| 4,693,248 | 9/1987 | Failla | |
| 4,711,232 | 12/1987 | Fischer et al. | 411/71 |
| 4,711,234 | 12/1987 | Vives et al. | |
| 4,716,893 | 1/1988 | Fischer et al. | |
| 4,738,255 | 4/1988 | Goble et al. | |
| 4,741,330 | 5/1988 | Hayhurst | |
| 4,744,793 | 5/1988 | Parr et al. | 623/13 |
| 4,772,286 | 9/1988 | Goble et al. | 623/13 |
| 4,776,329 | 10/1988 | Treharne | |
| 4,778,468 | 10/1988 | Hunt et al. | 623/16 |
| 4,790,850 | 12/1988 | Dunn et al. | 623/13 |
| 4,834,752 | 5/1989 | Van Kampen | 623/13 |
| 4,851,005 | 7/1989 | Hunt et al. | 623/18 |
| 4,863,476 | 9/1989 | Shepperd | 623/17 |
| 4,870,957 | 10/1989 | Goble et al. | |
| 4,888,022 | 12/1989 | Huebsch | 623/22 |
| 4,895,150 | 1/1990 | Isaacson et al. | |
| 4,927,421 | 5/1990 | Goble et al. | 606/73 |
| 4,960,420 | 10/1990 | Goble et al. | 606/72 |
| 4,997,433 | 3/1991 | Goble et al. | 606/64 |
| 5,037,422 | 8/1991 | Hayhurst et al. | 606/72 |
| 5,108,431 | 4/1992 | Mansat et al. | 623/13 |
| 5,129,902 | 7/1992 | Goble et al. | 606/65 |
| 5,147,362 | 9/1992 | Goble | 606/72 |
| 5,152,790 | 10/1992 | Rosenberg et al. | 623/13 |
| 5,176,682 | 1/1993 | Chow | 606/232 |
| 5,211,647 | 5/1993 | Schmieding | 606/73 |
| 5,236,445 | 8/1993 | Hayhurst et al. | 606/73 |
| 5,258,016 | 11/1993 | Dipoto et al. | 606/75 |
| 5,268,001 | 12/1993 | Nicholson et al. | 606/72 |

FOREIGN PATENT DOCUMENTS

| | | | |
|---|---|---|---|
| 52573 | 2/1993 | European Pat. Off. | 606/72 |
| 1082415 | 3/1984 | U.S.S.R. | 606/75 |

OTHER PUBLICATIONS

Charles L. Beck, Jr., Lonnie E. Paulos and Thomas D. Rosenberg, "Anterior Cruciate Ligament Reconstruction with the Endoscopic Technique," pp. 86–98, *Operative Techniques in Orthopaedics*, vol. 2, Apr. 1992.

*Primary Examiner*—Guy V. Tucker
*Assistant Examiner*—Nancy Connolly Mulcare
*Attorney, Agent, or Firm*—Broadbent, Hulse, Pierce & Pate

[57] ABSTRACT

An endosteal anchoring device for urging a ligament graft against a bone surface comprising an anchoring body, a member for resisting slippage of the anchoring body into the periphery of a bone tunnel under ligament tension, a member for avoiding puncturing, piercing or tearing of cross-fibers of the ligament graft and a member for urging the ligament graft flush against the inner surface of the bone tunnel for accelerated healing.

16 Claims, 5 Drawing Sheets

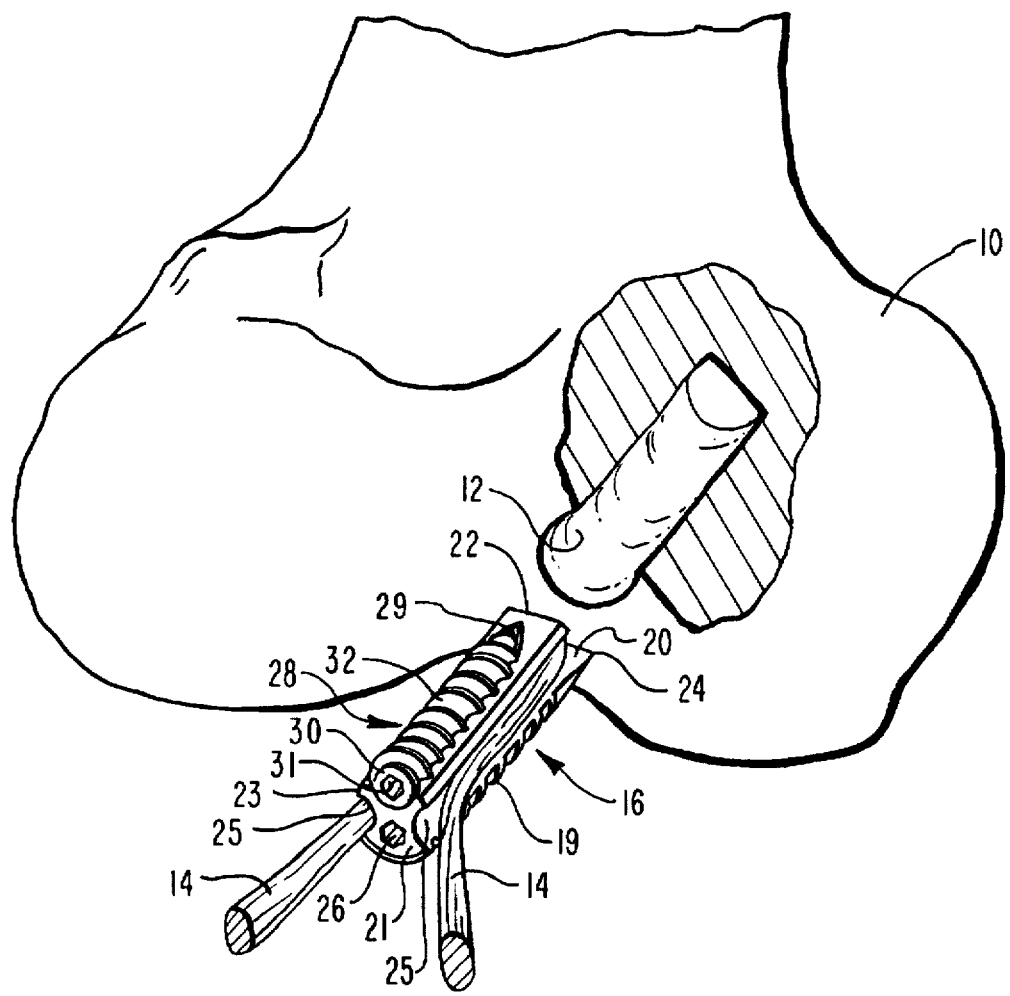
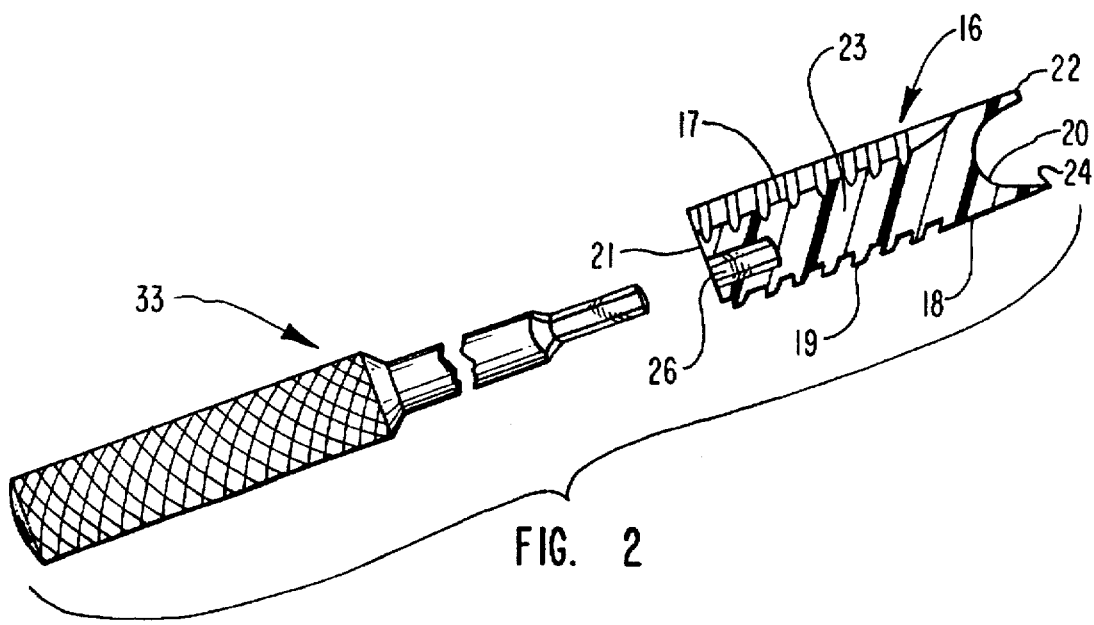

ENDOSTEAL ANCHORING DEVICE FOR URGING A LIGAMENT AGAINST A BONE SURFACE

This application is a continuation of my application Ser. No. 08/076,390, filed on Jun. 14, 1993 now abandoned for ENDOSTEAL ANCHORING DEVICE FOR URGING A LIGAMENT AGAINST A BONE SURFACE.

BACKGROUND

1. The Field of the Invention

This invention relates to orthopedic surgical procedures and, more particularly, to surgical devices involved in replacing, reconstructing or securing synthetic or biological connective tissue to a bone surface, such as, for example, attaching and maintaining a replacement anterior cruciate ligament (ACL) against a bone.

2. The Background Art

The knee joint is one of the strongest joints in the body because of the powerful ligaments which bind the femur and tibia together. Although the knee is vulnerable to injury as a result of the incongruence and proximity of its articular surfaces, the knee joint provides impressive stability due to the arrangement and interacting strength of its ligaments, muscles and tendons.

To a layman, the operation of the human knee resembles the actions of a hinge joint. However, in reality, the knee joint provides complicated mechanical movements and maneuverability far more complex than a simple hinge mechanism in regards to the rotation and gliding motions that may occur at the joint. In addition, the motions of flexing and extending the knee (and, in certain positions, the slight rotation inward and outward of the knee), require a very detailed structural configuration to facilitate the associated, refined mechanical movements of the knee joint.

Structurally, the knee joint comprises two discs of protective cartilage called menisci which partially cover the surfaces of the femur and the tibia. The menisci operate to reduce the friction and impact loading between the femur and the tibia during movement of the knee. The knee is also partly surrounded by a fibrous capsule lined with a synovial membrane which secrets a lubricating fluid. Strong ligaments on each side of the knee joint provide support to the joint and limit the side-to-side motion and joint opening of the knee. Fluid filled sacs called bursas are located above and below the patella (kneecap) and behind the knee providing a means of cushioning the kneecap upon impact and helping with joint lubrication. Moreover, the quadriceps run along the front of the thigh to straighten the knee, while the hamstring muscles run along the back of the thigh to bend the knee.

Two intra-articular ligaments of considerable strength, situated in the middle of the joint, are known as the cruciate ligaments. These ligaments are referred to as "cruciate ligaments" because they cross each other somewhat like the lines of the letter "X". The anterior and posterior cruciate ligaments receive their names in respect to the positioning of their attachment to the tibia. The primary function of the anterior cruciate ligament (ACL) is to provide a means for limiting hyperextension of the knee and preventing the backward sliding of the femur on the tibia plateau. The ACL also assists in limiting any medial rotation of the knee joint when the foot is solidly on the ground and the leg fixed in position. Conversely, the posterior cruciate ligament (PCL) primarily provides a means for preventing hyperflexion of the knee and preventing the femur from sliding forward on the superior tibial surface when the knee is flexed. Although the structure of the knee provides one of the strongest joints of the body, the knee is usually one of the most frequently injured joints. Athletes and persons who perform tasks requiring a great deal of body rotation are the most susceptible to serious ligament stressing and tearing at the knee joint. Consequently, the growing number of ligament injuries has given rise to considerable innovative activity within the area of orthopedic medicine in an effort to create surgical procedures and devices for replacing and reconstructing torn or dislocated ligaments.

Typically, the surgical procedures for ligament replacement and reconstruction involve tissues being grafted from one part of the body (autograft) to the original attachment sites of a torn or dislocated ligament. Once the ligament graft has been transplanted, it is then attached to the natural fixation sites of damaged ligament. For example, the replacement of an anterior cruciate ligament (ACL) may involve transplanting a portion of the patellar tendon to the attachment sites of the original ACL to assist in the reconstruction of the ACL in the knee joint.

The expectations of prior art orthopedic procedures typically relate to reconstructing or replacing natural ligaments so as to enable the recipient to return to his or her full range of activity in as short a period of time as possible. To that end, medical researchers have attempted to duplicate the relative parameters of strength, flexibility, and recovery found in natural ligaments of the body. Unfortunately, many of the prior art methods of reconstructing and replacing damaged ligaments have generally proven inadequate for immediately restoring full strength and stability to the involved joint. Furthermore, there has long been a problem of effectively fastening a ligament to a bone surface for the duration of a ligament's healing process, which process involves the ligament graft growing to an adjoining bone mass to restore mobility to the injured joint of an orthopedic patient.

Early ligament replacement procedures traditionally comprised extensive incisions and openings in the knee to attach a replacement ligament to bone surfaces at the fixation sites of the natural ligament. The ends of a grafted ligament were typically secured to exterior bone surfaces by driving stainless steel staples through or across the ligament and into the adjacent bone mass. The legs of the staples are generally adapted for piercing and penetrating tissue and bone mass, while maintaining a ligament at a specified connection site. Other various types of tissue fastening devices, such as channel clamps, were also designed by those skilled in the art. The channel clamps normally differed from the above-mentioned staple arrangement in that the channel clamp fixation devices comprise a plurality of components which do not require clinching in the conventional manner, as when setting a staple into a bone surface.

However, the use of stainless steel staples and other related fixation devices have a number of disadvantages. For example, piercing and puncturing of the ligament by the legs of the staples or other fixation devices may result in serious damage to the cross-fibers of the ligament or tissue. Such damage may cause weakening in the tensile strength of the ligament and result in tearing along the cross-fibers of the ligament under normal physical stress. When puncturing or tearing of cross-fibers occurs, the time required for the ligament to heal increases, which in turn results in a significant extension in the amount of time required to rehabilitate the knee joint before allowing the patient to return to normal daily activities.

To alleviate the disadvantages of cross-fiber damage exhibited by staples and other related fixation devices that puncture the body of the ligament, improvements in the types of surgical devices and techniques were developed by those skilled in the art. For example, one such technique involves drilling a hole through a bone to form a channel wherein an anchoring device may be inserted with a ligament graft attached thereto. Typically, the ligament is maintained at a fixation site in the bone channel by passing a suture through one end of the ligament graft and thereafter attaching the other end of the suture to an anchoring device positioned at the face of the opening of the channel in the bone mass. However, problems materialize when trying to secure the threads of the suture to the anchoring device when a physician is working in restricted or confined areas. As a result, combination drilling devices operably coupled to suture anchors were designed for dealing with ligament placement problems in areas of restricted maneuverability.

After a period of time, significant disadvantages emerged wherein a number of the ligament grafts retained in bone mass by the combination drilling/anchor devices began to rupture and tear at their fixation sites around the area where the ligament was in direct contact with the sharp outer edges of the opening of the channel formed in the bone. For example, as replacement ligaments tolerate the stress and strain associated with normal physical activity, the ligament generally begins to fatigue when wearing against the sharp outer edges of a bone channel opening. This form of fatigue typically causes significant damage to the ligament by tearing or cutting into ligament cross-fibers, thus, weakening the connection of the replacement ligament at its reattachment site. Consequently, after a period of time, cross-fiber fatigue, commonly known as "sun-dial" wear, may further result in dislocating the replacement ligament from its original fixation site.

Because of the significant disadvantages associated with "sun-dial" wear or fatigue on replacement ligaments, improved surgical procedures were developed offering arthroscopic-assisted techniques typically including the formation of passages or tunnels through bone mass, wherein natural or synthetic ligaments may be inserted. After the ligament graft has been inserted into the bone tunnel, a ligament anchoring device is generally used to connect one end of a ligament to the exterior of the bone mass. The anchoring means generally requires that the replacement ligament end or ends be advanced beyond the bone tunnel, with each ligament end being bent and secured onto the exterior surface of the bone. Nevertheless, unfavorable disadvantages of ligament bending was observed by those skilled in the art as typically resulting in a force concentration at the location of the ligament bend generally causing the cross-fibers of the ligament to weaken, potentially subjecting the ligament to the possibility of further tearing or rupturing, as in the case of ligament sundial wear.

In response to the problems associated with maintaining a replacement ligament graft at a fixation site, additional devices and techniques were developed offering means whereby a ligament may be retained within a bone tunnel by an endosteal fixation device, such as, for example, an interference screw. The threads of the interference screw are typically bored into the bone tunnel for recessed engagement with the attached bone and one end of the ligament graft, while maintaining the ligament at a fixation site within the bone tunnel. Unfortunately, puncturing, piercing and possible tearing generally results to the cross-fibers of the ligament when the ligament is in direct engagement with the sharp threads of the interference screw. In addition, the interference screw typically requires a ligament replacement graft to be attached to its original bone.

During flexion or extension of the ligament, tension loads tend to act against the fixation site of the ligament generally causing strain on the ligament against its fixation site. Under such strain, the facing of the threads of the interference screw generally effect a pinching or piercing of the ligament which may cause tearing or dislocation of the replacement ligament under the stress associated with normal physical activities. Consequently, when a grafted ligament suffers cross-fiber damage due to puncturing, piercing or tearing, the healing period for the ligament dramatically increases, thereby in effect, increasing the rehabilitation time for the patient to recover.

One of the preferred methods employed by a number of skilled physicians when repairing torn or dislocated ligaments involves the harvesting of an autograft patella tendon bone block for incorporation into a femoral socket. Although the use of a patella tendon bone block provides a number of advantages, especially when dealing with fixation of the replacement ligament, the harvesting of a patella bone block typically results in extensive morbidity to the knee joint, requiring a considerable amount of time for the knee joint to heal, before a patient can resume any normal physical activity.

As illustrated by the foregoing summary, efforts are continuously being made to improve the graft types, surgical methods and devices used in replacing and reconstructing torn or dislocated ligaments so as to make the process more efficient and effective. However, significant disadvantages remain with all the presently known devices and methods offered by the prior art.

BRIEF SUMMARY AND OBJECTS OF THE INVENTION

In view of the foregoing, it is a primary object of the present invention to provide an endosteal anchoring device for urging a ligament against a bone surface without piercing, puncturing or tearing the cross-fibers of the ligament.

Another object of the present invention is to provide an endosteal anchoring device and endoscopic technique for urging a ligament against a bone surface minimizing the possibility of sun-dial wear on the replacement ligament.

It is also an object of the present invention to provide an endosteal anchoring device for urging a ligament against a bone surface which is capable of retaining a ligament at a fixation site within a bone tunnel, while restricting the anchor member from slippage under the stress and strain of normal physical activity.

It is an other object of the present invention to provide an endosteal anchoring device for urging a ligament against a bone surface while dispensing a desired amount of surface area compression on the ligament graft allowing collateral circulation into the tissue for promotion of the ligament healing to the bone.

Further, it is an object of the present invention to provide an endosteal anchoring device for urging a ligament against a bone surface which is easily adjustable during a surgical procedure so that proper tension, nearly duplicating the natural condition of the torn or dislocated ligament, can be sustained on the replacement ligament graft.

It is a still further object of the present invention to provide an endosteal anchoring device and method for urging a ligament against a bone surface whereby a ligament graft may be retained flush against the surface of a bone tunnel to facilitate a decrease in the amount of healing time for the ligament graft, while substantially decreasing its morbidity rate.

It is also a still further object of the present invention to provide an endosteal anchoring device and method for urging a ligament against a bone surface while simulating the fixation advantages associated with a patella tendon bone block, without incurring excessive morbidity to the knee joint.

Consistent with the foregoing objects, and in accordance with the invention as embodied and broadly described herein, a permanent or bio-absorbable endosteal anchoring device for urging a replacement ligament against a bone surface is disclosed as comprising an anchoring body, a means for resisting slippage of the anchoring body within a bone tunnel under ligament tension, a means for avoiding puncturing, piercing or tearing of ligament cross-fibers, and a means for urging the ligament graft flush against the inner surface of the bone tunnel to accelerate the healing of the replacement ligament.

BRIEF DESCRIPTION OF THE DRAWINGS

The foregoing and other objects and features of the present invention will become more fully apparent from the following description and appended claims, taken in conjunction with the accompanying drawings. Understanding that these drawings depict only typical embodiments of the invention and are, therefore, not to be considered limiting of its scope, the invention will be described with additional specificity and detail through use of accompanying drawings in which:

FIG. 1 is a perspective view illustrating one presently preferred embodiment of the endosteal anchoring device of the present invention;

FIG. 2 is a cross-sectional side view of the embodiment of FIG. 1 showing an opening in the endosteal anchor body wherein a directional driver is inserted;

DETAILED DESCRIPTION OF THE PREFERRED EMBODIMENTS

Figure 3:
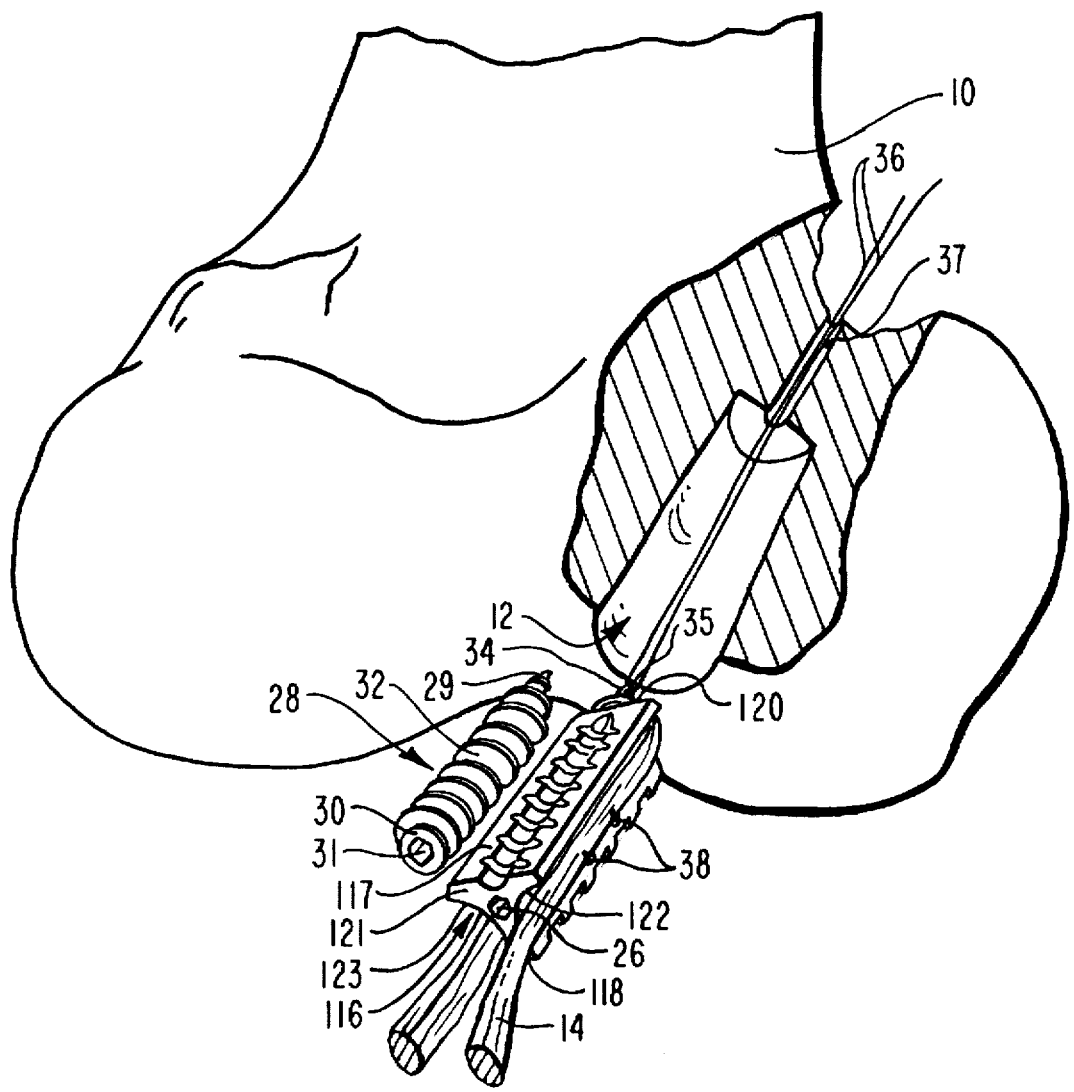
FIG. 3 is a perspective view illustrating a second presently preferred embodiment of the endosteal anchoring device of the present invention.

It will be readily understood that the components of the present invention, as generally described and illustrated in the Figures herein, could be arranged and designed in a wide variety of different configurations. Thus, the following more detailed description of the preferred embodiments of the endosteal anchoring device and method of the present invention, as represented in FIGS. 1 through 10, is not intended to limit the scope of the invention, as claimed, but it is merely representative of the presently preferred embodiments of the invention.

The presently preferred embodiments of the invention will be best understood by reference to the drawings, wherein like parts are designated by like numerals throughout.

When reconstructing or replacing a torn or dislocated ligament, care should be taken to provide a means for connecting a ligament to its predetermined connection site and maintaining it firmly thereto. Generally, surgical procedures involve either the use of natural biological tissue grafts or prosthetic ligaments, simulated to mimic the parameters of strength, flexibility and positioning of the natural ligament it replaces.

As shown in FIGS. 1 and 2, to accommodate a ligament graft 14 to a fixation site, the present invention offers a device for urging a ligament 14 against the peripheral surface of a tunnel 12 formed within a bone 10, by implementing an endoscopic technique designed primarily for use with arthroscopic assistance. When reconstructing or replacing a torn or dislocated ligament, particularly the anterior cruciate ligament (ACL) of the knee, a bone tunnel 12 is generally formed in the femur and/or tibia for positioning the natural or synthetic ligament graft 14 therein.

The preferred method provided by the present invention for replacing or reconstructing dislocated ligaments utilizes an endosteal anchor member 16, formed of plastic, bone, stainless steel or any other suitable material. The endosteal anchor member 16 consists of a rigid anchor body 23 having an upper ridge 22 and a lower ridge 24 displaying a groove 25 integrally formed therebetween. Preferably, the endosteal anchoring device is manufactured from a material suitable for sterilization and human implantation, and comprised of either a permanent non-biodegradable material or a bio-degradable material capable of being absorbed by the body while maintaining the essential rigid qualities required to accommodate its anchoring functions.

The upper ridge 22 and the lower ridge 24 of the endosteal anchor member 16 extend slightly beyond the first end 20 of the anchor body 23. Oriented between the upper ridge 22 and the lower ridge 24 is an elongated groove 25 having a semi-circular cross-sectional area wherein a ligament graft 14 may be positioned. At the first end 20 of the anchor body 23, a curvilinear indentation is formed between the upper ridge 22 and the lower ridge 24 providing a front semi-circular facing for the elongated groove 25.

Preferably, the ligament graft 14 is encircled around the first end 20 of the endosteal anchor member 16 and positioned within the surface area of the front curvilinear facing of the groove 25. The ligament 14 may then be looped around the perimeter of the anchor body 23 and positioned within the linear cross-sectional area of the groove 25. The first end of the ligament graft 14 is preferably advanced back upon itself and fastened to a connection site on the body of the ligament 14 to approximate a looped configuration.

The positioning of the ligament graft 14 within the surface area of the groove 25 provides a means of locking the ligament at a specified fixation site when the anchor body 23 is positioned within the periphery of the bone tunnel 12. Looping the ligament 14 around the first end 20 of the body 23 of the endosteal anchor member 16 and positioning the ligament 14 within the cross-sectional area of the groove 25, provides a means whereby restricting excessive compression on the ligament 14 when the endosteal anchor member 16 is positioned within the periphery of the bone tunnel 12. By restricting the movement of the ligament 14 within the bone tunnel 12, bone ingrowth occurs more readily, rather than fibrous formations, which significantly decreases the healing time required for the replacement ligament.

Preferably positioned and integrally formed along the upper exterior surface 17 of the anchor body 23 are multiple tapped grooves which provide a means for intersecting with the threads 32 of a threaded insertion member 28. Being substantially circular and preferably comprised of stainless steel or any other suitable material, the threaded insertion member 28 exhibits a first end 29, preferably formed with a bullet nose, and a second end 30. Spirally threaded from the first end 29 to the second end 30 of the threaded insertion member 28, the threads 32 provide a circular diameter which is substantially compatible with the tapped grooves in the upper surface 17 of the anchor body 23. Recessed within the second end 31 of the threaded insertion member 28 is a slot 31 wherein a complimentary turning device is inserted to aid in rotating the threaded insertion member 28 into the periphery of the bone tunnel 12 for communication with the upper exterior surface 17 of the endosteal anchor member 16.

As shown in FIG. 2, recessed within the second end 21 of the anchor body 23 is an opening 26 wherein a directional driver 33 may be inserted to position the endosteal anchor member 16 being operably coupled to a looped ligament 14 within the periphery of the bone tunnel 12. Preferably, the face of the opening 26 and the tip of the directional driver 33 are formed having a complimentary hexagonal shape. It will be readily appreciated, however, that other shapes or configurations of the opening 26 and the tip of the directional driver 33 are also possible.

As illustrated in FIGS. 1 and 2, positioned along the lower surface 18 of the anchor body 23 and extending therefrom, are a plurality of projecting members 19 which provide a means of resisting slippage of the endosteal anchor member 16 within the bone tunnel 12 after being placed therein. The projecting members 19 of the anchor body 23 are herein illustrated as displaying a curvilinear shape, however, other shapes or configurations are readily possible.

In practice, the ligament graft 14 is looped around the front facing of the groove 25 at the first end 20 of the endosteal anchor member 16, thereafter looped back within the cross-sectional area of the groove 25 encircling the anchor body 23. The directional driver 33 may be inserted into the recessed opening 26 formed within the second end 21 of the anchor body 23 for positioning the anchor body 23 within the bone tunnel 12. The threaded insertion member 28 is then rotatably introduced along the tapped upper surface 17 of the anchor body 23 while self-tapping into the adjacent surface area of the bone tunnel 12.

The combination of the threaded insertion member 28 and the features of the endosteal anchor member 16 provides a means of locking the ligament graft 14 at a fixation site. In addition, the projecting members 19 which emerge from the lower surface 18 of the anchor body 23 provide a means for restricting slippage of the anchoring device within the bone tunnel 12 under the ligament stress and strain associated with normal physical activity.

Figure 4:
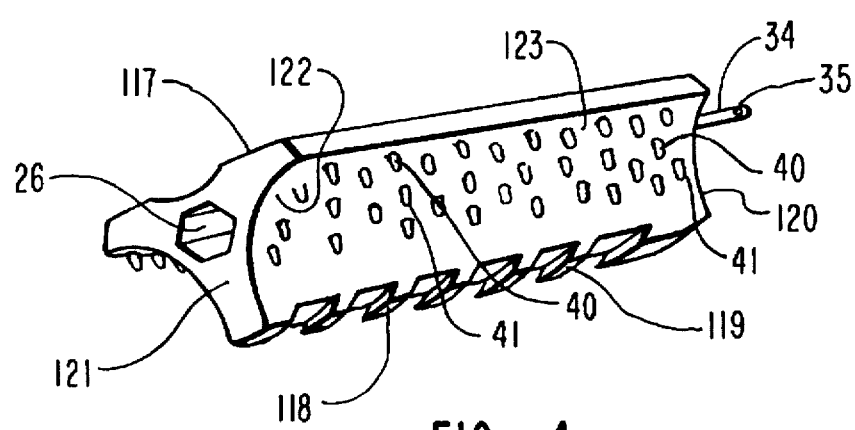
FIG. 4 is a cross-sectional view of FIG. 3 displaying a plurality of urging members.

Illustrated in FIGS. 3 and 4 is a second presently preferred embodiment of the endosteal anchoring device for urging a ligament against a bone surface consisting of an endosteal anchoring member 116, formed of plastic, bone, stainless steel or any other suitable material, comprising a substantially elongated anchor body 123. Preferably, the endosteal anchoring device is manufactured from a material suitable for sterilization and human implantation, and comprised of either a permanent non-biodegradable material or a biodegradable material capable of being absorbed by the body while maintaining the essential rigid qualities required to accommodate its anchoring functions.

The anchor body 123 exhibits an upper ridge 122 extending the linear length of the anchor body 123 from its first end 120 to its second end 121. Preferably, the anchor body 123 is tapered and gradually decreases in surface area from the upper ridge 122 to the lower surface 118. The surface area between the upper ridge 122 and the lower surface 118 on both sides of the tapered anchor body 123 provides a substantially curved cross-sectional area wherein a ligament graft 14 may be positioned.

Integrally formed within the second end 121 of the anchor body 123 is an opening 26 wherein a directional driver 33 may be inserted to introduce and position the endosteal anchor member 116 within the bone tunnel 12 at a designated fixation site. Preferably, the opening 26 at the second end 121 of the anchor body 123 and the insertion tip of the directional driver are formed having a complimentary hexagonal shape. However, it will be readily appreciated that other shapes or configurations are also possible.

An alternative means for introducing the endosteal anchor member 116 into the bone tunnel 12 offered by the present embodiment may involve the utilization of a post member 34 extending parallel and slightly beyond the first end 120 of the anchor body 123. The projecting post 34 preferably resembles a small circular stock or projecting rod and provides a means for positioning the endosteal anchor member 116 against the ligament graft 14 within a bone tunnel 12. At the distal end of the post 34 is an eyelet 35 wherein the end of a suture 36 is introduced and passed therethrough. After attaching the suture 36 to the post member 34, the leading ends of the suture 36 are pulled through a channel 37 having a significantly reduced diameter in comparison to the diameter of the bone tunnel. Situated beyond the bone tunnel 12 and extending to the outer exterior surface of the bone 10, the channel 37 provides an opening through the bone mass 10 wherein the suture 36 being attached to the projecting post 34 can be pulled to introduce the endosteal anchor member 116 into the inner surface area of the bone tunnel 12. When using a blind-end technique, the post 34 of the endosteal anchor member 216 provides a means whereby the anchor body 223 can be inserted into the bone tunnel 12 without having to form a tunnel through the entire body of the bone exposing at least two openings.

As shown in FIG. 3, a ligament graft 14 may be passed up and over the post member 34 at the first end 120 of the anchor body 123. Preferably, the ligament 14 is looped around the perimeter of the anchor body 123 and positioned within the tapered surface areas of the anchor body 123 established beneath the cross-sectional area of the upper ridge 122.

Integrally formed within the tapered sides of the anchor body 123 is at least one through-bore 38 forming an opening which extends transversely through the anchor body 123 from one side to the other. Preferably, a suture is inserted through the through-bore 38 and passed through the looped ligament graft 14 placed within the tapered surface area of the anchor body 123. Positioned between the first end 120 and second 121 end of the endosteal anchor member 116, the through-bore provides an opening wherein a suture may be passed to secure the ligament graft 14 to the endosteal anchor member 116.

As best shown in FIG. 4, an alternative means for retaining the looped ligament graft within the tapered surface area of the anchor body 123, comprises a plurality of urging members 40 projecting substantially outward from the underside of the upper ridge 122 and along the upper surface area of the sides of the anchor body 123. Preferably aligned in rows or oriented in criss-cross patterns along the anchor body 123, the urging members 40 display rounded or angularly blunt tips 41 which engage and maintain the looped ligament graft within the tapered surface area of the anchor body 123 without piercing, puncturing or tearing the cross-fibers of the ligament.

Preferably positioned and integrally formed along the upper exterior surface 117 of the anchor body 123 are multiple tapped grooves which provide a means for intersecting with the threads 32 of a threaded insertion member 28, as best illustrated in FIG. 3. Being substantially circular and preferably comprised of stainless steel or any other suitable material, the threaded insertion member 28 exhibits a first end 29, preferably formed with a bullet nose, and a second end 30. Recessed within the second end 31 of the threaded insertion member 28 is a slot 31 wherein a complimentary turning device is inserted to aid in rotating the threaded insertion member 28 into communication with the upper exterior surface 117 of the endosteal anchor member 116 and the peripheral wall of the bone tunnel 12. Spirally threaded from its first end 29 to its second end 30, the threads 32 of the threaded insertion member 28 provide a diameter substantially compatible with the tapped grooves in the upper surface 17 of the anchor body 23 and diameter of the bone tunnel 12, for positioning therebetween.

As illustrated in FIG. 4, extending from the lower surface 118 of the anchor body 123 are a plurality of projecting members 119 spaced apart a substantially equal distance from one another. The projecting members 119 of the anchor body 123 are herein illustrated as displaying a curvilinear shape, however, other shapes or configurations are readily possible.

In practice, the leading end of the ligament graft 14 may be positioned beneath the upper ridge 122 and along one side of the tapered anchor body 123, passed up and over the projecting post 34 located at the first end 120 of the anchor body 123 and further looped around the other tapered side of the anchor body 123 while providing a means for limiting compression on the ligament 14 as the ligament 14 is locked at its fixation site within the bone tunnel 12. Consequently, by restricting the movement of the ligament 14 within the bone tunnel 12, bone ingrowth occurs rather than fibrous formations, which may significantly decrease the healing time required for the replacement ligament 14.

When positioning the endosteal anchor member 116 within the bone tunnel 12, a directional driver may be inserted into the recessed opening 26 formed within the second end 121 of the anchor body 123, or a projecting post 34 may be used in combination with a leading suture 36 passed through the eyelet 35 at the distal end of the post 34 to pull the anchor body 123 into the bone tunnel 12 using a blind-end technique. Once the endosteal anchor member 116 is positioned within the bone tunnel 12, the threaded insertion member 28 is rotatably introduced along the tapped upper surface 117 of the anchor body 123, wherein the threaded insertion member 28 provides a means for self-tapping into the adjacent surface area of the bone tunnel 12. Accordingly, the combination of the threaded insertion member 28 and the features of the endosteal anchor member 116 provides a means of locking the ligament graft 14 at its fixation site. In concert, the projecting members 119 emerging from the lower surface 118 of the anchor body 123 provides a means for restricting slippage of the anchoring device within the bone tunnel 12.

Figure 5:
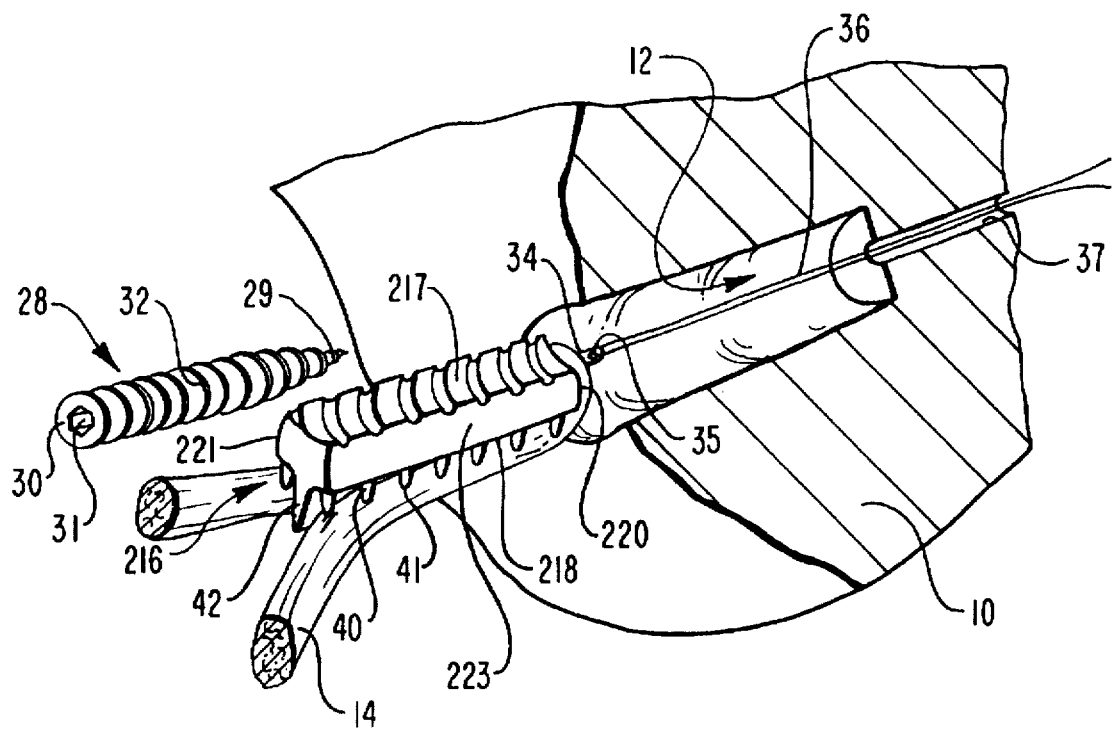
FIG. 5 is a perspective view illustrating a third presently preferred embodiment of the endosteal anchoring device of the present invention.
Figure 6:
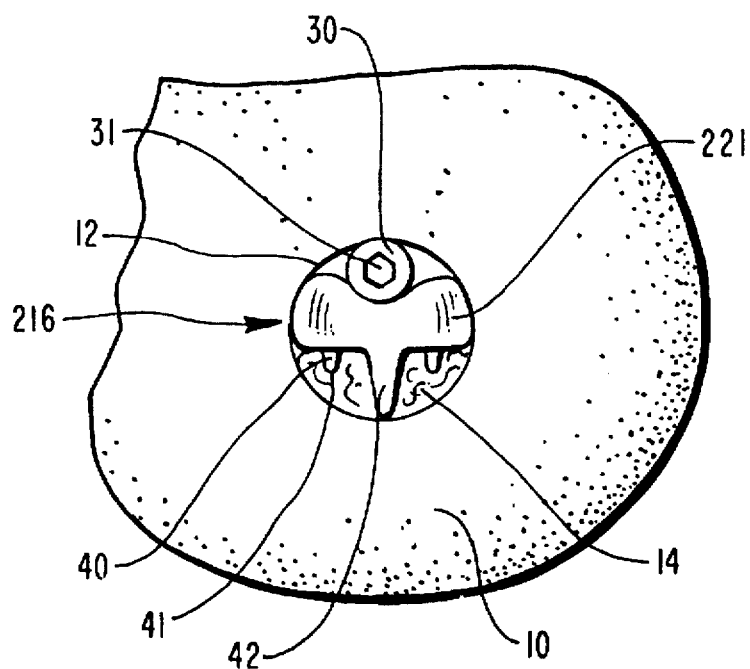
FIG. 6 is an end elevational view of the embodiment of FIG. 5 showing an endosteal anchoring device urging a ligament against the inner surface of a bone tunnel while engaging a cooperating threaded member.

Shown in FIGS. 5 and 6 is a third presently preferred embodiment of the endosteal anchoring device for urging a ligament against a bone surface comprising an endosteal anchoring member 216, formed of plastic, bone, stainless steel or any other suitable material. The endosteal anchor member 216 consists of a substantially elongated cylindrical body 223 having an upper exterior surface 217 and a wedge member 42 extending from a lower surface 218 of the anchor body 223. Preferably, the endosteal anchoring device is manufactured from a material suitable for sterilization and human implantation, and comprised of either a permanent non-biodegradable material or a bio-degradable material capable of being absorbed by the body while maintaining the essential rigid qualities required to accommodate its anchoring functions.

Projecting substantially outward from the lower surface 218 of the anchor body 223, is an elongated wedge member 42 disposed in alignment with the anchor body 223 and extending the linear length of the endosteal anchor member 216 from a first end 220 to a second end 221. Preferably arranged in rows or oriented in criss-cross patterns, a plurality of urging members 40 may be positioned along the lower exterior surface 218 of the anchor body 223, adjacent the peripheral sides of the elongated wedge member 42. While projecting substantially outward from the lower exterior surface 218 of the anchor body 223, the urging members 40 display rounded or angularly blunt tips 41 which discourage piercing, puncturing or tearing of ligament cross-fibers, when the endosteal anchor member 216 is in direct engagement with the ligament graft 14.

As shown in FIG. 5, extending parallel and slightly beyond the first end 220 of the anchor body 223 protrudes a post member 34 resembling a small circular stock or projecting rod. The post member 34 provides a means for positioning the endosteal anchor member 216 within a bone tunnel 12 to retain a ligament graft 14 at its fixation site. Accordingly, an eyelet 35 is provided in the distal end of the post member 34 wherethrough a suture 36 may be introduced. After passing the suture 36 through the eyelet 35 of the post member 34 and securing it thereto, the suture 36 is drawn through a small channel 37 formed in the bone 10 that extends beyond the periphery of the bone tunnel 12 out to the exterior surface of the bone mass 10. When using a blind-end technique, the post 34 of the endosteal anchor member 216 provides a means whereby the anchor body 223 can be inserted into the bone tunnel 12 without having to form a tunnel through the entire body of the bone exposing at least two openings.

In practice, one end of the ligament 14 may be introduced along either side of the elongated wedge member 42, passed up and over the projecting post 34 which is located at the first end 220 of the anchor body 223, and further positioned along the opposing side of the wedge member 42. After encircling the perimeter of the anchor body 223, the leading end of the ligament 14 may be attached to the body of the ligament graft 14 by a suture, or some other conventional means, conforming the ligament into a loop configuration.

The placement of the ligament 14 around the first end 220 of the anchor body and against the sides of the wedge member 42 provides a means for limiting compression on the ligament 14 when locked at its fixation site within the bone tunnel 12. Consequently, by restricting the movement of the ligament 14 within the bone tunnel 12, bone ingrowth occurs, rather than fibrous formations, significantly decreasing the healing time required for the ligament graft 14.

Preferably positioned and integrally formed along the upper exterior surface 217 of the anchor body 223 are multiple tapped grooves which provide a means for intersecting with the threads 32 of a threaded insertion member 28. Being substantially circular and preferably comprised of stainless steel or any other suitable material, the threaded insertion member 28 exhibits a first end 29, preferably formed with a bullet nose, and a second end 30. Recessed within the second end 221 of the threaded insertion member 28 is a slot 31 wherein a complimentary turning device or directional driver is inserted to aid in rotating the threaded insertion member 28 in communication with the upper exterior surface 217 of the endosteal anchor member 216 and the peripheral wall of the bone tunnel 12. Spirally threaded from its first end 29 to its second end 30, the threads 32 of the threaded insertion member 28 provide a diameter substantially compatible with the tapped grooves in the upper surface 217 of the anchor body 223 and the bone tunnel 12, for positioning therebetween.

As illustrated in FIGS. 5 and 6, an endosteal anchoring member 216 is inserted into a bone tunnel 12 and positioned against a ligament graft 14. A complimentary turning member is inserted into the slot 31 recessed in the second end 30 of the threaded insertion member 28 for rotating the threads 32 of the threaded insertion member 28 into the tapped grooves of the anchoring body 223, and for self-tapping the insertion member 28 into the inner surface of the bone tunnel 12. In concert, the features of the endosteal anchor member 216, the cooperating threaded member 28 and the wedge member 42 in concert with the urging members 40 provide a means for firmly locking a replacement ligament 14 flush against the inner surface of the bone tunnel 12. The force concentration of the endosteal anchor member 216 and the cooperating threaded member 28 provides a means for resisting slippage of the anchor body 223 from the periphery of the bone tunnel 12.

Figure 7:
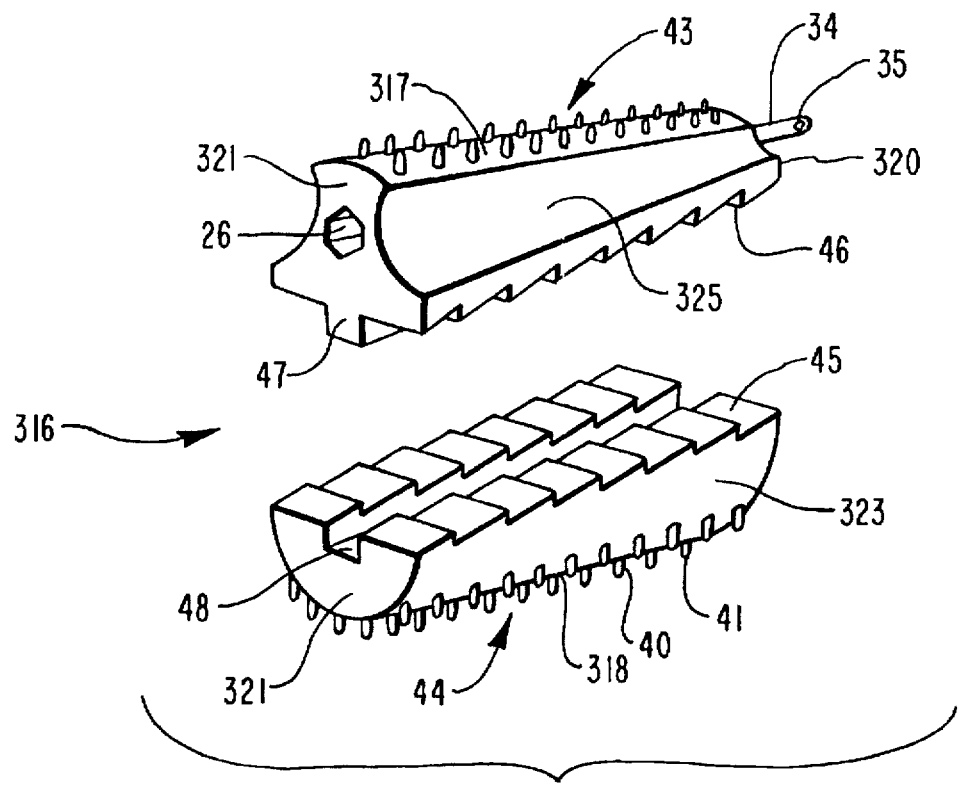
FIG. 7 is a perspective view illustrating a fourth presently preferred embodiment of the endosteal anchoring device of the present invention.
Figure 8:
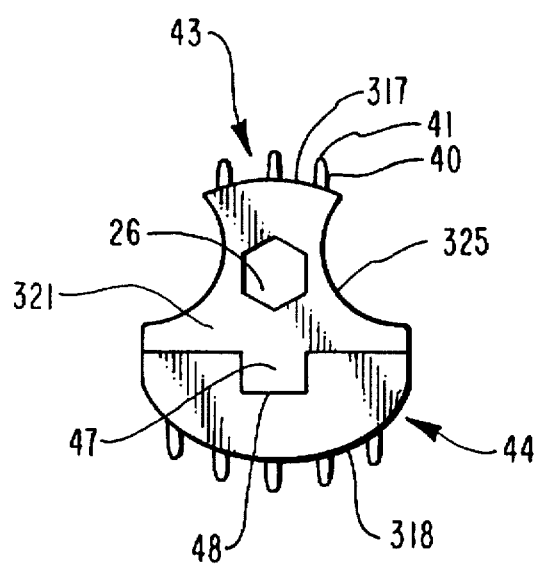
FIG. 8 is an end elevational view of the embodiment of FIG. 7 showing the placement of the two wedge-shaped components in association with each other.

Shown in FIGS. 7 and 8 is a fourth presently preferred embodiment of the endosteal anchoring system for urging a ligament against a bone surface comprising an endosteal anchoring device 316, formed of plastic, bone, stainless steel or any other suitable material, having at least two wedge-shaped components 43 and 44 which together comprise a substantially tubular body 323. Preferably, the endosteal anchoring device is manufactured from a material suitable for sterilization and human implantation, and comprised of either a permanent non-biodegradable material or a biodegradable material capable of being absorbed by the body while maintaining the essential rigid qualities required to accommodate its anchoring functions.

An inner surface 45 extending from a first end 320 to a second end 321 of the first component 43 is preferably formed with a plurality of interlocking ridges 46 projecting substantially outward from the exterior of the inner surface 45. The inner surface of the second component 44 may also display a plurality of interlocking ridges 46 which project substantially outward from its inner surface 45, but which are positioned in such a way, so as to be disposed at an opposing angle with the ridges 46 of the first component 43. When the first and the second component are positioned in alignment with one another, the opposing surface areas of the ridges 46 of the first component 43 and the ridges 46 of the second component 44 become interlocked with one another forming the substantially tubular body 323 of the endosteal anchor member 316. The one-way movement of the first wedge-shaped component 43 along the interlocking ridges 46 of the second component 44 creates a considerable urging force which maintains the endosteal anchor device 316 in communication with the inner peripheral surface of a bone tunnel when placed therein.

Integrally formed on each side of the first component 43 is a substantially semi-circular elongated groove 325. Extending from the first end 320 to the second end 321 of the anchor body 323, the elongated groove 325 provides a recessed surface area along the sides of the endosteal anchor device 316 wherein a ligament can be positioned. Preferably, a ligament graft is maintained within the cross-sectional area of the groove 325 located on one side of the first component 43, looped up and over a protruding post 34 located on the first end 320 of the endosteal anchor device 316, and further positioned within the cross-sectional area of the groove 325 located on the opposing sides of the first component 43. Preferably, the lead end of the ligament graft is advanced back upon itself, where the ligament may be sutured to a connection site on the body of the ligament while forming a loop configuration.

The upper exterior surface 317 of the first wedge-shaped component 43 and the lower exterior surface 318 of the second wedge-shaped component 44 may be provided with a plurality of urging members 40 which project substantially outward therefrom. Preferably, the urging members 40 exhibit rounded or angularly blunt tips 41 on their distal ends to provide a means of resisting slippage of the endosteal anchor device 316 when positioned within a bone tunnel. The urging members 40 are arranged in rows or oriented in criss-cross patterns and provide constant pressure against the periphery of the bone tunnel to maintain the endosteal anchor member 316 from slippage under normal ligament stress and strain.

As best shown in FIG. 7, substantially parallel to the inner surface 45 of the second component 44, and embedded therein is a substantially elongated rectangular canal 48 extending from the first end 320 to the second end 321 of the anchor body 323. The elongated canal 48 of the second component 44 engages a complimentary raised key member 47 which protrudes substantially outward from the inner surface 45 of the first component 43. The raised key member 47 of the first component 43 and the elongated linear canal 48 of the second component 44 provide a means for guiding the two components 43 and 44 into combination when placed into the bone tunnel to form the endosteal anchor device 316.

Parallel and slightly beyond the first end 320 of the first wedge-shaped component 43 extends a post member 34, resembling a small circular stock or projecting rod. The post member 34 provides a means for positioning the endosteal anchoring device 316 into a bone tunnel and for retaining a replacement ligament at its fixation site. An eyelet 35 may be provided in the distal end of the post member 34 wherethrough a suture may be introduced. Once the suture is passed through the eyelet 35 of the post member 34 and secured thereto, the suture is further introduced through a small channel formed through the bone, extending beyond the periphery of the bone tunnel and to the outer exterior surface area of the bone. Using a blind-end technique, the post 34 of the endosteal anchor device 316 provides a means whereby the anchor body 323 can be inserted into the bone tunnel, without having to drill a tunnel having at least two openings formed in the bone.

As shown in FIG. 8, at the second end 321 of the first wedge-shaped components 43 is a recessed slotted opening 26 wherein a directional driver may be inserted for positioning the first component 43 within the bone tunnel. It will readily be appreciated, however, that other shapes or configurations of the slotted opening 26 and the tip of the directional driver are readily possible.

Preferably in practice, the second wedge-shaped component 44 is positioned within the bone tunnel, while a ligament is looped around the first wedge-shaped component 43 and positioned within the recessed area of the groove 325. The raised key member 47 of the first component 43 is aligned and integrally positioned within the elongated rectangular canal 48 of the second component 43 to be slideably engaged therein. As the surface of the ridges 46 of the inner surface 45 of the first component 43 slides along the surface of the ridges 46 of the inner surface 45 of the second component 44, both the first and second components 43 and 44 become interlocked, thereby providing an interactive means for securing the anchor device and the ligament within the bone tunnel. As the components 43 and 44 become interlocked, the urging members 40, positioned on the upper exterior surface 317 and the lower exterior surface 318, provide a means of forced compression on the surface area of the bone tunnel while maintaining the looped ligament flush against the bone at a fixation site.

Figure 9:
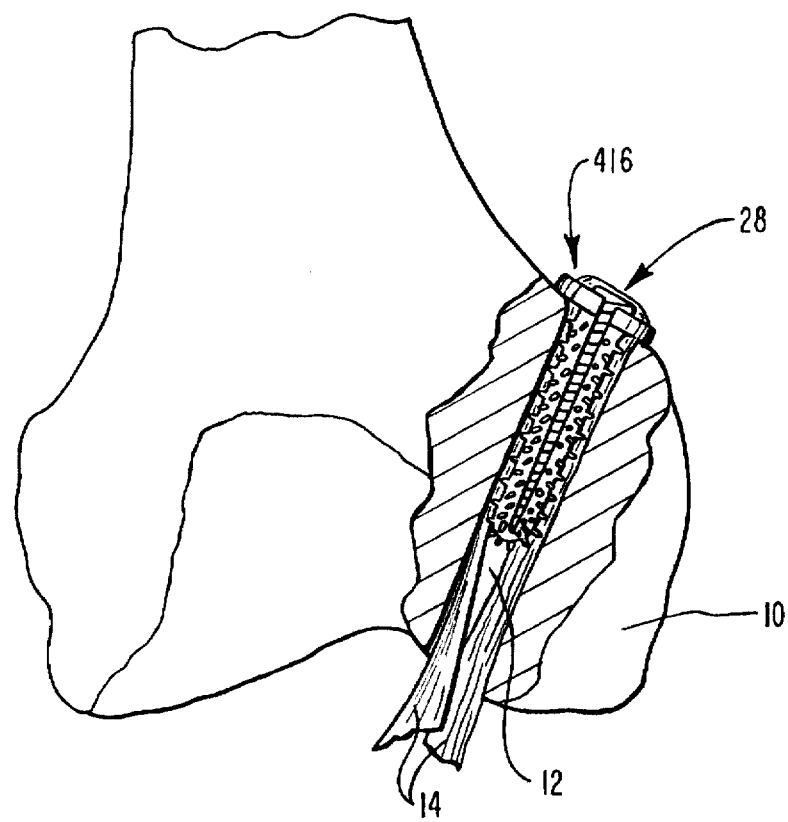
FIG. 9 is a perspective view illustrating a fifth presently preferred embodiment of the endosteal anchoring device of the present invention positioned within a bone tunnel.
Figure 10:
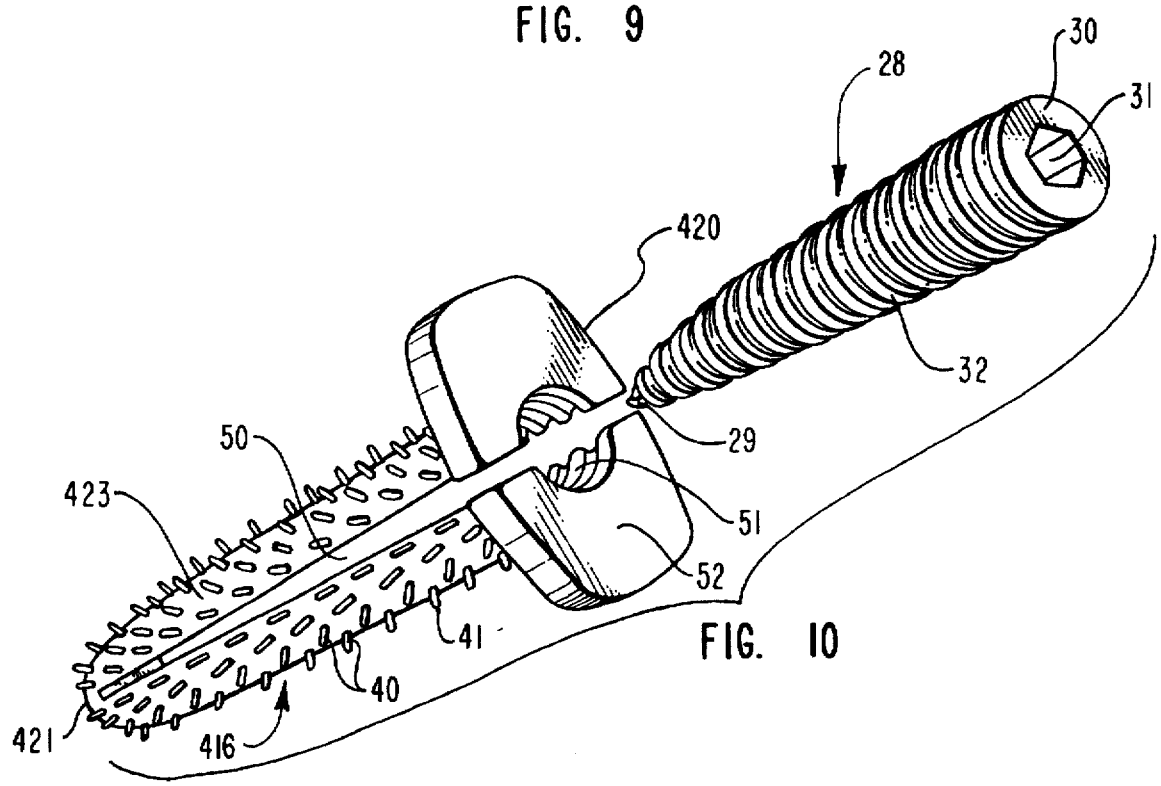
FIG. 10 is a cross-sectional view of the embodiment of FIG. 9.

Illustrated in FIGS. 9 and 10 is a fifth presently preferred embodiment of the endosteal anchoring device for urging a ligament against a bone surface comprising an endosteal anchor member 416, formed of plastic, bone, stainless steel or any other suitable material. The endosteal anchor member 416 consists of a substantially elongated cylindrical body 423 with at least two extending wings 52 projecting substantially outward and perpendicular to a first end 420 of the anchoring body 423. Preferably, the endosteal anchoring device is manufactured from a material suitable for sterilization and human implantation, and comprised of either a permanent non-biodegradable material or a bio-degradable material capable of being absorbed by the body while maintaining the essential rigid qualities required to accommodate its anchoring functions.

The extending wings 52 of the endosteal anchor member 416 are preferably rectangular or disc-shaped and project substantially outward a distance greater than the diameter of the opening of a bone tunnel 12. It will readily be appreciated, however, that other shapes or configurations for the extending wings 52 are readily possible. As illustrated in FIG. 9, when the body 423 of the endosteal anchor member 416 is introduced into the bone tunnel 12, the extending wings 52 of the anchor body 423, being significantly greater in length and width than the diameter of the opening in the bone tunnel 12, engage the exterior surface area of the bone 10 adjacent the bone tunnel opening. Consequently, the risk of the anchor body 423 slipping into the periphery of the bone tunnel 12 is minimized due to the counteracting forces provided by extending wings 52 acting against the surface area of the bone 10.

Preferably, the exterior surface area of the anchor body 423 is substantially covered with a plurality of urging members 40 projecting substantially outward from the exterior surface. Aligned in rows or in criss-cross patterns, the urging members 40 exhibit rounded or angular blunt tips 41 to discourage piercing, puncturing, or tearing of the ligament cross-fibers as the ligament experiences the stress and strain of normal physical activity.

Preferably formed in a looped configuration, the leading end of the ligament graft 14 is introduced along one side of the anchor body 423, passed up and over the surface area of the extending wings 52 of the endosteal anchor member 416, and further passed across the opposing side of the anchor body 423. In practice, the tips 41 of the urging members 40 apply pressure against concentrated areas of the ligament graft 14 to retain the ligament 14 firmly at a fixation site. While the tips 41 of the urging members 40 maintain the ligament graft 14 flush against the inner surface of the bone tunnel 12, circulation to the transplanted ligament graft 14 is improved without damaging any cross-fibers of the ligament.

As illustrated in FIG. 10, recessed between the extending wings 52 of the anchor body 416 is an opening 51, preferably tapped, projecting inwardly into an annular canal 50 extending the length of the cylindrical anchor body 423 from its first end 420 to its second end 421. The cross-sectional diameter of the canal 50 at the first end 420 of the endosteal anchor member 416 begins to taper radially, becoming progressively smaller towards the second end 421 of the anchor body 423, while preferably forming a slight inner conical cavity therein.

A threaded insertion member 28, being substantially circular and preferably comprised of stainless steel or any other suitable material, may be introduced into the opening 51 at the first end 420 of the endosteal anchoring member 416. The first end 29 of the threaded insertion member 28, preferably comprising a bullet nose, is introduced into the opening 51 of the endosteal anchoring member 416 to be further rotatably inserted into the inner surface area of the annular canal 50.

Spirally threaded from its first end 29 to its second end 30, the insertion member 28 has threads 32 displaying a diameter substantially compatible with the inner surface of the annular canal 50 formed within the anchor body 423. The second end 30 of the threaded insertion member 28 may be formed with a recessed slot 31 wherein a complimentary turning device may be inserted to aid in introducing the threaded insertion member 28 into the periphery of the annular canal 50.

As described above, since the annular canal 50 is preferably tapered radially from the first end 420 to the second end 421 of the anchor body 423, when the threaded insertion member 28 is introduced therein, the diameter of insertion member threads 32, remaining somewhat constant from its first end 29 to its second end 30, begins to enlarge the annular canal 50 along a divisional split, disposed in alignment with the anchor body 423. Preferably, the expansion of the annular canal 50 causes the anchor body 423 to extend outwardly against the inner surface of the bone tunnel 12 concentrating an association therewith. Upon insertion of the threaded member 28 into the opening 51 of the annular canal 50, the extending wings 52 of the endosteal anchoring member 416 also begin to expand while providing a means for retaining the anchor body 423 from further slippage into the bone tunnel 12.

Although the endosteal anchoring device of the present invention may be used at any location in the body which requires the fixation of a ligament graft, it is preferably employed during an endoscopic technique used with arthroscopic assistance for replacement and reconstruction of an anterior cruciate ligament (ACL) of the knee, which in practice, appears to significantly decrease the level of morbidity of the ligament graft. The method or technique provided by the present invention allows for isometric placement of a variety of tissue graft types into tibial and femoral bone tunnels drilled under arthroscopic control.

Preferably, the endoscopic technique is performed by first establishing anteromedial and anterolateral portals in the knee for diagnosis and operative arthroscopy. Once a diagnosis and the pathology of the knee has been adequately studied, the ACL reconstruction may be performed.

A tissue or ligament graft (autograft or allograft) is harvested and prepared for attachment at the fixation site of the torn or dislocated ACL. The patellar tendon may be grafted to replace the ACL, however, other tendons, such as the Achilles tendon or hamstrings may be used to reconstruct and replace dislocated ligaments without incurring the serious disadvantages associated with a patella tendon bone block concerning morbidity to the knee joint.

With an arthroscope in the anterolateral portal, the tibial anatomic site is studied and a guide pin inserted to mark the proposed site for the drilling of a tibial tunnel. Accordingly, the tibial tunnel is drilled by passing an endoscopic drill bit over the already inserted guide pin.

When identifying a femoral attachment site, the isometric and mechanical behavior of the selected femoral attachment site for the ligament graft should be assessed prior to formation of the femoral tunnel, since changes in the placement of the replacement ligament will have significant effects on the behavior of the isometric properties of the ligament graft. Once the femoral attachment site is selected, the guide pin is further inserted and passed through the tibial tunnel while the knee is flexed at a substantially 90 degree angle, to mark the proposed fixation site on the femur for the ligament graft. An endoscopic drill bit is manually passed over the guide pin through the tibial tunnel, across the joint and into the femur to drill a femoral tunnel.

Consequently, the guide pin is removed and the femoral tunnel irrigated wherein a small Beathe-type pin is placed. A suture is attached to the ends of the transplanted ligament graft and used to advance the graft through the tibial tunnel, across the joint and into the femoral tunnel. Once the graft is properly oriented in the tunnel, it is seated with tension on the guide suture until the bone-tendon junction is flush with the opening of the femoral tunnel. A blind-end technique, as discussed above in reference to the preferred embodiments of the endosteal anchoring device, may also be considered as a viable option when applying the arthroscopic-assisted and endoscopic techniques offered by the present invention.

The ligament graft is maintained against the inner surface of the femoral bone tunnel at the fixation site of the natural ligament using one of the preferred embodiments of the endosteal anchoring device of the present invention. Preferably, the endosteal anchoring device and the threaded insertion member is manufactured from a material that is suitable for sterilization and human implantation, which may comprise a permanent material or a bio-degradable material capable of being absorbed by the body while maintaining sufficient rigid qualities to accommodate its prescribed functions.

The body of the endosteal anchoring device is inserted and positioned within the bone tunnel, while the knee is flexed at a substantially 90 degree angle, and under direct arthroscopic visualization. The endosteal anchoring device of the present invention, as discussed above, provides a means for resisting slippage of the anchoring body from its placement within the bone tunnel.

The endosteal anchoring device of the present invention provides a means whereby a ligament graft may be looped around the body of the endosteal anchor member and retained within the cross-sectional area of an adjacent groove. The positioning of the ligament graft within the groove of the anchor member provides a means of locking the ligament at a fixation site, and restricts excessive ligament compression of the ligament against the surface of the bone tunnel. By restricting ligament movement within the bone tunnel, bone ingrowth occurs rather than fibrous formations, which significantly increases the healing rate of the replacement ligament.

The endosteal anchoring device of the present invention also provides a plurality of urging members that extend substantially outward from the exterior surface of the anchoring body that provide a means for urging the ligament graft flush against the inner surface of the bone tunnel without piercing, puncturing or tearing the cross-fibers of the ligament. Moreover, after positioning the endosteal anchoring device against the ligament graft in the bone tunnel and after the proper tensioning of the ligament is achieved, the incisions are then closed and a sterile dressing applied thereto.

While preferred embodiments of the endosteal anchoring device have been shown and described herein, the present invention may be embodied in other specific forms without departing from its spirit or essential characteristics. The described embodiments are to be considered in all respects only as illustrative, and not restrictive. The scope of the invention is, therefore, indicated by the appended claims, rather than by the foregoing description. All changes which come within the meaning and range of equivalency of the claims are to be embraced within their scope.

What is claimed and desired to be secured by United States Letter Patent is:

1. An endosteal anchoring system for urging a ligament against a bone surface within a tunnel formed in a bone of a patient, the system comprising:

an anchor device, the anchor device having at least one end and an exterior surface comprising a surface area sufficient for disposing a portion of said ligament, said surface area providing a means for forcibly compressing said portion of the ligament against the bone surface of said tunnel;

said portion of said ligament engageably disposed in relation to the exterior surface of the anchor device being further disposed around said end of the anchor device;

a positioning member engageably disposed in relation to the anchor device, said positioning member providing a means for selectively positioning said anchor device within the tunnel; and means for securing the anchor device and said portion of the ligament disposed in a loop configuration around said exterior surface of said anchor device within the tunnel, said portion of the ligament being thereby urged directly against the bone surface within said tunnel.

2. An endosteal anchoring system for urging a ligament against a bone surface within a tunnel formed in a bone of a patient as defined in claim 1 wherein said positioning member comprises a directional driver.

3. An endosteal anchoring system for urging a ligament against a bone surface within a tunnel formed in a bone of a patient as defined in claim 1 wherein the anchor device comprises a first component and a second component, said first component and said second component having a plurality of interlocking members.

4. An endosteal anchoring system for urging a ligament against a bone surface within a tunnel formed in a bone of a patient as defined in claim 3 wherein said interlocking members provide means for interlocking said components together.

5. An endosteal anchoring device for urging a ligament against a bone surface within a tunnel formed in a bone of a patient as defined in claim 1 wherein said positioning member comprises at least one extending member projecting substantially outward from said end.

6. An endosteal anchoring system for urging a ligament against a bone surface within a tunnel formed in a bone of a patient as defined in claim 5 wherein said extending member comprises an eyelet for introducing a suture therethrough, said extending member in cooperation with said suture providing means for positioning said anchor member within said tunnel.

7. An endosteal anchoring system for urging a ligament against a bone surface within a tunnel formed in a bone of a patient, the system comprising:

an anchor device, the anchor device comprising a first component and a second component, said first component having at least one end and an exterior surface incorporating a groove, said first component and said second component comprising a plurality of interlocking members, whereby said interlocking members provide means for interlocking said components together;

said groove comprising a surface area sufficient for disposing a portion of said ligament, said surface area providing a means for forcibly compressing said portion of the ligament against the bone surface of said tunnel in a direction perpendicular to an axis of said anchor device;

said portion of said ligament disposed in relation to said groove of said first component being further disposed around said end of said first component;

a positioning member engageably disposed in relation to said anchor device, said positioning member providing a means for selectively positioning said anchor device within said tunnel; and means for securing said anchor member and said portion of said ligament disposed in a loop configuration around said anchor member within said tunnel, the ligament being thereby urged directly against the bone surface within said tunnel.

8. An endosteal anchoring system for urging a ligament against a bone surface within a tunnel formed in a bone of a patient as defined in claim 7 wherein said positioning member comprises a directional driver.

9. An endosteal anchoring device for urging a ligament against a bone surface within a tunnel formed in a bone of a patient as defined in claim 7 further comprising at least one extending member projecting substantially outward from said end.

10. An endosteal anchoring system for urging a ligament against a bone surface within a tunnel formed in a bone of a patient as defined in claim 9 wherein said extending member comprises an eyelet for introducing a suture therethrough, said extending member in cooperation with said suture providing means for introducing said anchor member within said bone tunnel.

11. An endosteal anchoring device for urging a ligament against a bone surface within a tunnel formed in a bone of a patient as defined in claim 7 wherein said means for securing said anchor member within said tunnel comprises a plurality of sustaining members.

12. An endoscopic technique for replacing or reconstructing a torn or dislocated ligament, the endoscopic technique comprising the steps of:

establishing portals in contiguous bone mass for diagnosis and operative arthroscopy;

forming a tunnel within the bone mass;

maintaining a portion of the ligament in a loop configuration around an exterior surface of an anchor device, said exterior surface comprising a surface area sufficient for forcibly compressing said portion of said ligament against an internal wall of said tunnel in a direction perpendicular to an axis of said anchor device;

positioning the anchor device and the ligament operably coupled thereto within the tunnel; and securing the anchor device and said portion of the ligament within the tunnel, thereby urging said portion of the ligament in direct contact against said internal wall of said tunnel.

13. A method as defined in claim 12 wherein said anchor device comprises a first component and a second component, said first component having a raised key member and said second component having an elongated canal, whereby disposing said raised key member within the elongated canal provides means for guiding said first and second components into alignment and interlocking said first and second components together.

14. A method as defined in claim 12 wherein forming a tunnel within the bone mass further comprises inserting a guide pin through the portals to mark a location for drilling the tunnel and passing an endoscopic drill bit over the guide pin to form said tunnel.

15. An endoscopic technique used with arthroscopic assistance for repairing or reconstructing a torn or dislocated anterior cruciate ligament, the endoscopic technique comprising the steps of:

establishing anteromedial and anterolateral portals in contiguous bone mass for diagnosis and operative arthroscopy;

inserting a guide pin through the portals to mark a location for drilling a tibial tunnel;

passing an endoscopic drill bit over the guide pin to form the tibial tunnel;

inserting the guide pin through the tibial tunnel to select a location for drilling a femoral tunnel;

passing the endoscopic drill bit over the guide pin to form the femoral tunnel;

irrigating said tunnels;

maintaining the ligament in relation to an exterior surface of an endosteal anchor device and disposing said ligament around at least one end of said anchor device in a loop configuration, said exterior surface of said anchor device comprising a surface area sufficient for forcibly compressing said portion of the ligament against the bone surface of said femoral tunnel in a direction perpendicular to an axis of said anchor device;

inserting the endosteal anchor device into the femoral bone tunnel;

positioning the endosteal anchor device and the ligament operably coupled thereto within the femoral tunnel; and securing the anchor device and said portion of the ligament within the femoral tunnel, thereby urging said portion of the ligament in direct contact against the bone within said femoral tunnel to promote healing.

16. A method as defined in claim 15 wherein said anchor device comprises a first component and a second component, said first component having a raised key member and said second component having an elongated canal, whereby disposing said raised key member within the elongated canal provides means for guiding said first and second components into alignment and interlocking said first and second components together.

* * * * *

UNITED STATES PATENT AND TRADEMARK OFFICE
CERTIFICATE OF CORRECTION

PATENT NO.   :   5,632,748

DATED        :   May 7, 1997

INVENTOR(S)  :   Charles L. Beck, Jr. et al.

It is certified that error appears in the above-identified patent and that said Letters Patent is hereby corrected as shown below:

In column 8, line 66, please delete "121 end", and insert therefore -- end 121 --.

Signed and Sealed this

Thirtieth Day of September, 1997

Attest:

BRUCE LEHMAN

Attesting Officer          Commissioner of Patents and Trademarks